United States Patent
Bala

(10) Patent No.: US 9,489,627 B2
(45) Date of Patent: Nov. 8, 2016

(54) HYBRID CLUSTERING FOR DATA ANALYTICS

(71) Applicant: Bottomline Technologies (DE), Inc., Portsmouth, NH (US)

(72) Inventor: Jerzy W. Bala, Potomac Falls, VA (US)

(73) Assignee: Bottomline Technologies (DE), Inc., Portsmouth, NH (US)

(*) Notice: Subject to any disclaimer, the term of this patent is extended or adjusted under 35 U.S.C. 154(b) by 545 days.

(21) Appl. No.: 13/932,299

(22) Filed: Jul. 1, 2013

(65) Prior Publication Data

US 2014/0143186 A1    May 22, 2014

Related U.S. Application Data

(60) Provisional application No. 61/727,815, filed on Nov. 19, 2012, provisional application No. 61/776,021, filed on Mar. 11, 2013.

(51) Int. Cl.
*G06F 15/18* (2006.01)
*G06N 5/02* (2006.01)
*G06F 19/24* (2011.01)

(52) U.S. Cl.
CPC .............. *G06N 5/025* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 7,092,941 B1 | 8/2006 | Campos | |
| 7,308,436 B2 | 12/2007 | Bala et al. | |
| 8,229,875 B2 | 7/2012 | Roychowdhury | |
| 8,229,876 B2 | 7/2012 | Roychowdhury | |
| 2008/0104007 A1 | 5/2008 | Bala | |
| 2009/0307176 A1* | 12/2009 | Jeong | G06F 17/30702 706/52 |
| 2010/0066540 A1* | 3/2010 | Theobald | G06Q 50/24 340/573.1 |
| 2012/0041683 A1* | 2/2012 | Vaske | G06F 19/12 702/19 |
| 2013/0071816 A1 | 3/2013 | Singh et al. | |
| 2013/0231974 A1* | 9/2013 | Harris | G06Q 30/0201 705/7.29 |

OTHER PUBLICATIONS

Bansal, Nikhil, Avrim Blum, and Shuchi Chawla. "Correlation clustering." Machine Learning 56.1-3 (2004): 89-113.*
Finley, Thomas, and Thorsten Joachims. "Supervised clustering with support vector machines." Proceedings of the 22nd international conference on Machine learning, ACM, 2005.*
Meia et al., Comparing clusterings-an information based distance, Journal of Multivariate Analysis 98 (2007) 873-895.

* cited by examiner

*Primary Examiner* — Kakali Chaki
*Assistant Examiner* — Kevin W Figueroa
(74) *Attorney, Agent, or Firm* — Renner, Otto, Boisselle and Sklar LLP

(57) ABSTRACT

The invention includes methods and systems for analyzing data to determine trends in the data and to identify outliers. The methods and systems include a learning algorithm whereby a data space is co-populated with artificial, evenly distributed data, and then the data space is carved into smaller portions whereupon the number of real and artificial data points are compared. Through an iterative process, clusters having less than evenly distributed real data are discarded. Additionally, a final quality control measurement is used to merge clusters that are too similar to be meaningful. The invention is widely applicable to data analytics, generally, including financial transactions, retail sales, elections, and sports.

20 Claims, 8 Drawing Sheets

Rule Training $N$ = number of negative data points, initially distributed uniformly through space $$N_1 = \frac{N*K}{(K+M)} \qquad N_2 = \frac{N*M}{(K+M)}$$

If after specialization cut,
$N$ < number of positive points,
increase $N$ to match number of positive points

HYBRID CLUSTERING FOR DATA ANALYTICS

RELATED APPLICATIONS

This application claims priority to U.S. Provisional Patent Application No. 61/727,815 filed Nov. 19, 2012 and U.S. Provisional Patent Application No. 61/776,021 filed Mar. 11, 2013, both of which are incorporated by reference in their entireties.

FIELD OF THE INVENTION

The invention relates to methods and systems for identifying trends and outlier data within a data set. The invention can be applied to a variety of fields, including gene sequencing and bioanalytics, medical imaging, fraud detection, buyer analytics, and sports analytics.

BACKGROUND

With the increasing availability of data storage and computing power, it is feasible for a variety of businesses and entities to collect, store, and analyze large amounts of data related their activities. For example, web retailers, stock brokers, and even gamblers "crunch the numbers," to gain an advantage over their competition. In some instances, an entity is looking for a trend, such as sales correlated with a new web layout. In other instances, an entity is looking for an outlier, indicating an activity, asset, or performance that has gone overlooked. The outlier might be bad: indicating a genetic propensity for a disease, an underperforming business unit, or insider trading. Alternatively, the outlier might be good: indicating a teaching style that is boosting class scores or a minor-league pitcher that will succeed in the big leagues.

As the amount of data collected by businesses increases, the efficiency of automated techniques for analyzing that data should increase in order to allow for timely analysis. Furthermore, most items or events may be characterized by many different markers such as time, place, cost, date, color, style, etc., etc., resulting in huge multivariable data sets. Looking for trends, while taking all of these variables into consideration, is a formidable task. That is, even with today's powerful computing resources, identifying outliers from a data set of thousands of events, where each event has twenty or more variables, can require substantial time and expense.

Techniques such as clustering can help to reduce the time and complexity of identifying outliers (and trends) by binning data with similar characteristics. Clustering typically involves assigning multidimensional data into subsets, or clusters, so that the observations of the same cluster are similar in some sense. Once the clusters are identified and filled, the size and relationship of the clusters can be compared in order to spot trends (big clusters) or outliers (clusters that are "far away" from the others).

Typically, clustering achieves its most profound results when using classifications that are unsupervised. That is, the data is not labeled ahead of time ("fraudulent", "cancer", or "profitable") and used as a training data set to direct classification of similar data. In these examples, the data, itself, becomes the source of the labels, and the technique can uncover unexpected correlations that represent overlooked opportunities. By looking at the data holistically, including multiple dimensions, it is possible to identify groupings that were not appreciated previously. For example, unsupervised clustering is able to segment customers with similar behaviors so that marketers can target specific, not previously identified segments with the highly customized content. Such cluster analysis driven marketing campaigns have already proved their effectiveness.

Nonetheless, even "unsupervised" clustering must have rules to direct the clustering toward a valuable result. Without some rules, the clustering will have no significance.

Of course, adding the complexity of unsupervised classification to a large multivariable data set can make meaningful analyses untenable because of the massive computational resources needed. The cost of preparing and performing such analyses is prohibitive for most entities. Accordingly, there is a need for improved methods of unsupervised clustering that allow clusters to be efficiently determined. Such techniques allow more computing resources to be directed to comparing the clusters in order to identify trends and outliers.

SUMMARY

The invention provides methods and systems that implement an improved clustering technique to more efficiently identify clusters from a large, typically multivariate, data set. The rule-based clustering algorithm executes a machine learning process using data represented by two classes—real data (i.e., positive class data) and non-real and uniformly distributed simulated data (i.e., negative class data).

Like traditional supervised classification, the method uses the positive data examples to generate rules that discriminate the positive data examples from the negative data examples (negative class). Unlike traditional supervised classification, however, the positive data are not labeled to reinforce a particular outcome during the machine learning process. Rather, the clusters are allowed to self-form in a way that separates the clusters efficiently in the space spanned by the data. The clusters are then evaluated for quality using a two-part test that computes distances between a cluster centroid and the real data. Once the clusters are determined to be of high quality, the clusters can be compared to identify trends or outliers. The final clustering rules can also be used to predict outcomes of new events.

The invention additionally includes systems for executing the methods of the invention, e.g., including a computer readable medium, memory and a processor. The computer readable medium contains instructions that when executed cause the processor to obtain real data from the computer readable medium, identify a rule that clusters the real data using the algorithms described below, cluster the real data with the rule, and store the clustered real data on the computer readable medium. In an embodiment the rule is identified by performing steps including generating an evenly-distributed set of non-real data having an identical number of points as the real data, creating a database on the computer readable medium including the real data and the non-real data, executing a supervised machine-learning algorithm to determine a rule for clustering the real data and the non-real data together, evaluating the rule for clustering the real data by comparing the number of real data points and the number of non-real data points clustered by the rule, correlating the clustered real data with a data space, and validating the rule by comparing the location of the clustered real data with a location of other clustered real data.

Using the methods and systems of the invention, data of varying size and dimensions can be analyzed to identify trends, correlations, and outliers. Thus, the invention is applicable to discovering gene expression patterns, sequencing genes into groups/families, discovering different types of tissue in medical images, discovering population segments in survey data, recognizing communities within social networks, detecting features and objects in electronic images, market segmentation (e.g., to identify customers that share common purchase propensities), and profiling for audit compliance and/or fraud detection. Additional applications of the methods and systems of the invention will be identifiable based upon the disclosure and figures below.

DETAILED DESCRIPTION

Figure 1:
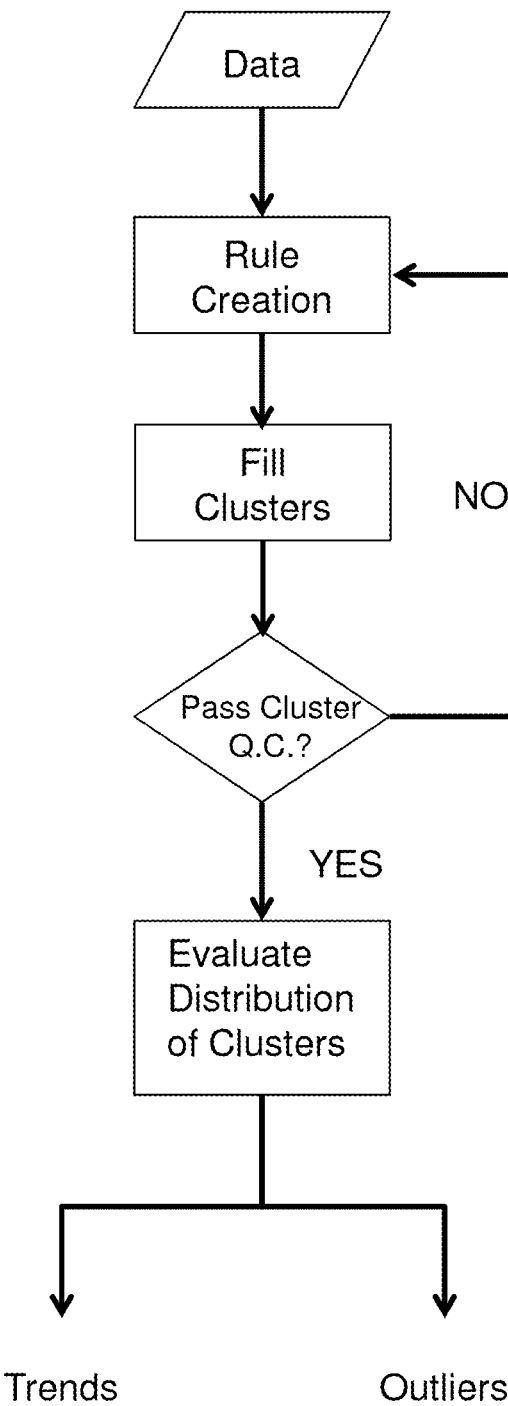
FIG. 1 is a flow chart showing an overview of the methods of the invention.

The invention relates generally to hybrid data clustering. Certain techniques are brought together and used in a single system to achieve the innovative hybrid data clustering including a rule-based based clustering algorithm, a distance-based inter and intra rule-based cluster computation algorithm, a cluster merging and rejection algorithm, a synthetic data representing empty spaces generation algorithm, and an empty space rule-based description generation algorithm.

The rule-based based clustering algorithm performs a supervised machine learning process using data represented by two classes—real data (positive class) and non-real and uniformly distributed simulated data (negative class). It uses the positive data examples to generate rules describing these examples and discriminating them from the negative data examples (negative class). The distance-based inter and intra rule-based cluster computation algorithm generates distance measures between centroids of the data points described by rules. The cluster merging and rejection algorithm uses computed distances to reject and/or merge clusters and the rejected clusters return their data (i.e., the data described by the rules) to the overall data pull for the next supervised machine learning iteration of the rule-based clustering algorithm. The synthetic data representing empty spaces generation algorithm simulates uniformly distributed negative data points. And the empty space rule-based description generation algorithm uses the simulated negative data examples (negative class) to generate rules describing these examples and discriminating them from the real data examples (positive class)

Analysis techniques such as k-means clustering can be used to determine a centroid of a cluster in the multi-dimensional space. Information about the location of the centroid in the multi-dimensional space can be used to determine general characteristics of data entry points forming the cluster. Such information can then be used by the business entity in making decisions related to the data mining task.

Data

The methods and systems of the invention can be used to analyze a wide variety of data. The data may include customer data for marketing campaign, financial audit data, and computer network log data.

For the methods and systems of the invention the data is represented as a set of examples (data points). An example may be anything that can be expressed in terms of representation language. An example can be a physical object, a situation, a cause, or a concept. Examples are usually described in an attribute-based representation as an n-tuple of attributes values, where n is a number of attributes. All n attributes define the clustering data space domain. A domain is associated with each attribute and is used to describe examples. The domain indicates the values the attribute may assume. The values in a domain may be unordered (or nominal) or ordered (or linear).

As rich data is now available from variety of sources, enterprises are now integrating of a wide range of data and in all forms. This enhanced ability to use data that is big in width (number of dimension) and depth (number of transactions) give many businesses unprecedented competitive advantages. For example, integrating medical claims data with clinical data for analysis results in more effectively managed patient care.

The methods and systems of the invention is especially suited for high dimensional data spaces. Traditional clustering techniques that depend on distance measures do not operate well in such data spaces.

Cluster Rules and Validation

Systems and methods of the invention include a hybrid clustering algorithm that generates rule-based clusters that order supplied data with informative grouping. Each group's similarities are expressed as a coherent pattern on a subset of dimensions. The coherent patterns, generally referred to as "rules," represent identified correlations among the data using a subset of data dimensions. In other words, the rules direct data to be grouped together if it exhibits similarities among the selected subset(s) of dimensions. The rules can be constructed using any of a number of machine learning algorithms, such as decision trees, generalization, or specialization rule covering algorithms.

The described clustering algorithm is different from traditional distance based clustering algorithms (e.g., k-means clustering) that rely heavily on the desired number of clusters. Such algorithms can be useful when the data is naturally clustered into a certain number of labels (i.e., because there are limited options, e.g., model of new car) or when the user defines which clusters are valuable, i.e., a structured search. However, as discussed in the Background, setting an optimal number of clusters for distance based clustering algorithms without other valuation information is difficult and computationally expensive.

The invention overcomes this difficulty by using a two-step hybrid clustering approach, described generally by the flowchart in FIG. 1. The first step involves iteratively assigning and evaluating sets of pattern based clusters. In the second step, additional distance based computations are performed on the data points as they are characterized by the clusters to generate cluster quality measures. These quality measures are used to accept, reject, merge, and/or rank discovered clusters. The second step reduces the number of redundant clusters and facilities effective pattern based clustering. This hybrid approach discovers objects that exhibit a coherent pattern and also the closeness of values of certain dimensions. The trade-off of pattern and distance based clustering represents one of the important aspects of the invention. Once the optimum cluster pattern has been established, the distribution of the clusters, and their weights can be evaluated to identify trends or outliers.

Figure 2:
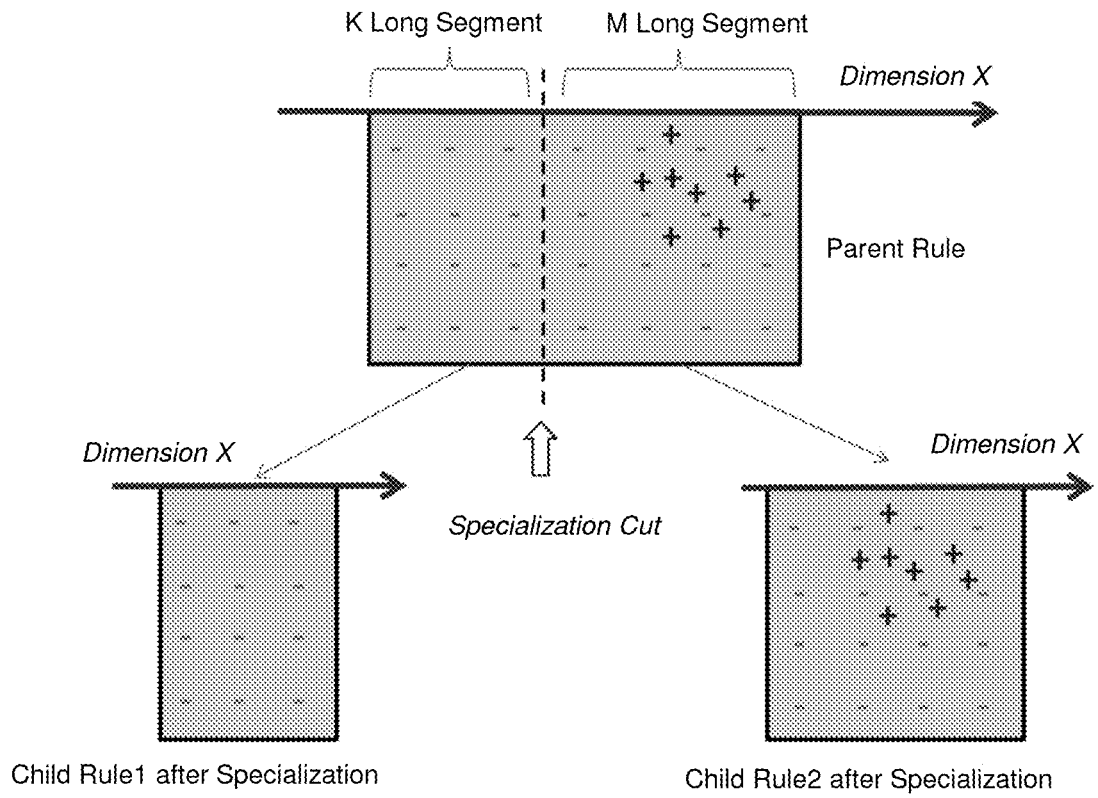
FIG. 2 illustrates the use of a specialization cut to divide a parent rule into two children rules.

The first processing run of the innovative hybrid clustering approach is based on the supervised learning method of rule induction, described in detail in FIG. 2. Initially, the algorithm regards each record (positive data examples) to have the same class annotation (i.e., class: "cluster"). This is the initial parent rule, a.k.a., the empty rule. The algorithm also assumes that the data space is uniformly populated with another type of data examples, called non-existing records (negative data points). The negative points are additionally assigned a different class annotation (i.e., class: "non-cluster"). This two-class scenario redefines the clustering task to be the supervised learning task of partitioning the data space into data dense regions ("clusters") and empty (sparse) regions ("non-clusters"). This algorithm is shown graphically in FIG. 2.

The algorithm of generating synthetic data examples performs the following calculations to estimate the number of synthetic data examples needed for each new cluster.

For the empty rule (i.e., the first rule to be specialized that represents a whole data representation space) the number of synthetic data examples is equal to the number of all positive data examples. This is simply a definition. It is trivial to fill the space with evenly distributed negative data points. After parent rule has been filled, the space is partitioned and then each partition (child rule) is evaluated as shown in FIG. 2.

As shown in FIG. 2, each child inherits some number of negative values because the previous space was filled before partition. The number of inherited negative data examples from its parent rule is used based on the proportion of specialization cuts (for numerical attributes) and a portion of a number of values defined by a symbolic attribute. The symbolic attribute can be randomly assigned, or it can be staged to generate successively smaller cluster spaces. Because the negative data was evenly distributed previously, the number of negative points is proportional to the dimension of the rule space (i.e., $N_1$ and $N_2$) as shown in FIG. 2.

FIG. 2 depicts the mechanism of splitting a parent rule into two child rules and the calculation of number of negative data points. The inherited number of negative data points (i.e., $N_1$ and N2) in each of the resulting rules is proportional to the negative data point in the parent rule (i.e., N) and weighted by the ratios of cut segments (K for Child Rule 1 and M for Child Rule 2) to the length of the rule for the dimension X (i.e., K+M). If the numbers of the inherited negative data points in either of the child rules are smaller than the numbers of positive data points then the negative data points are reset to the number of positive data points (i.e., the number of positive data points inherited directly from the parent rule). Depending upon the partition, the child may or may not contain positive data. See, for example, Child Rule 1 vs. Child Rule 2 in FIG. 2.

Figure 3:
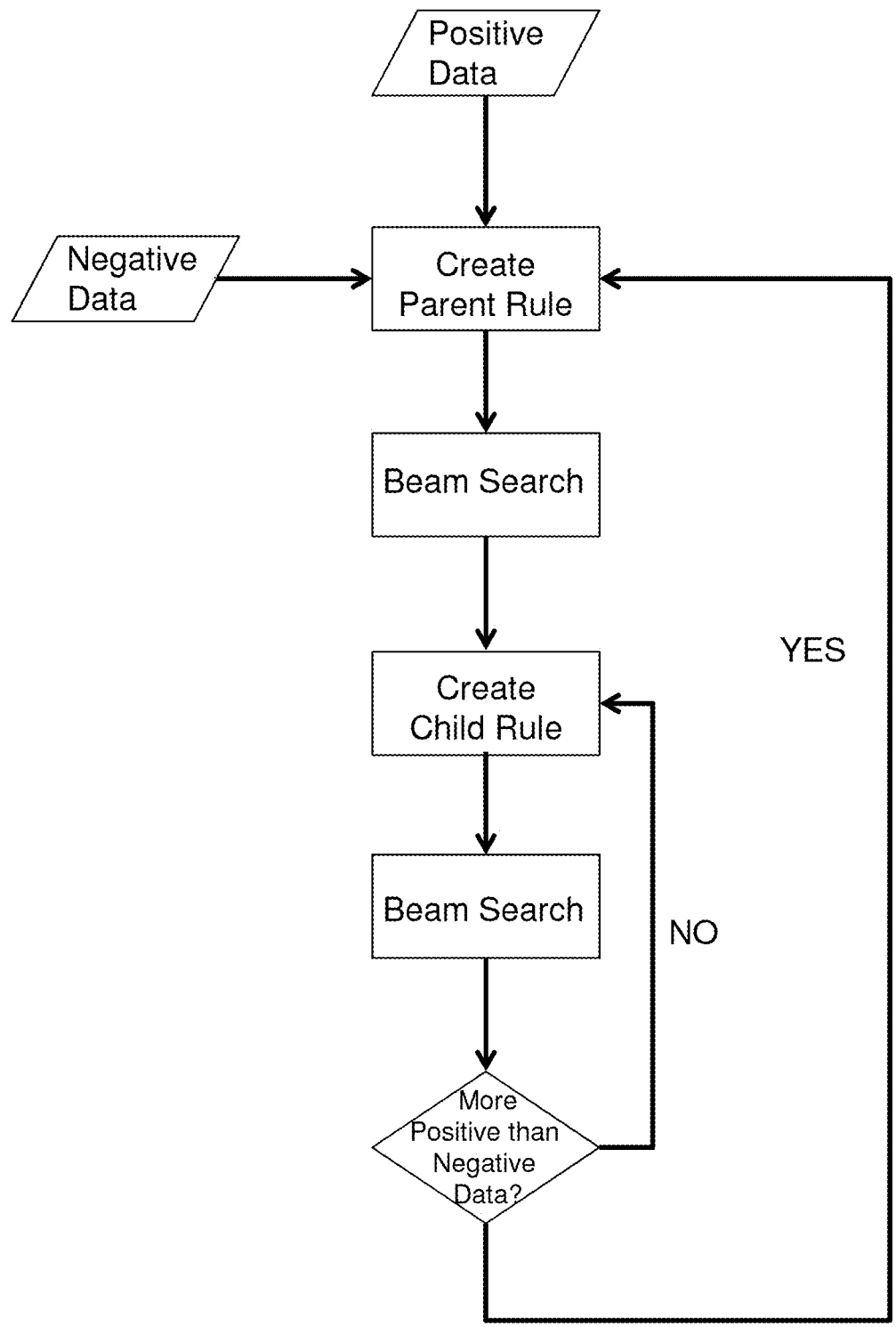
FIG. 3 is a flow chart showing the hybrid clustering technique of the invention.

Each child rule is then evaluated by comparing the number of positive data points to the number of negative data points. If the number of positive data points inherited from the parent rule is less than the number of negative data points inherited, the specialization cut was unsuccessful. That is, the number of positive data points captured by the cluster is actually worse than if the positive data points had been uniformly distributed based upon the empty rule. However, rules that inherit more positive than negative data represent a successful specialization cut. At this point, the child rule is repopulated with enough negative data points to match the number of inherited positive data points, and the process repeats, as shown in FIG. 3. This process is continued until child rules reach their minimum recall (% of positive data points) or minimum precision (% of negative data points covered by a rule).

When executed in an iterative fashion, as described in FIG. 3, adding uniformly distributed negative data points helps isolate the clusters of positive data points, while reinforcing the choice of denser positive data groupings. Given a representation space defined by a set of attributes (features) and positive and negative examples (data points) annotated with decision classes (e.g., positive/target and negative/non-target decision classes) the algorithm can quickly determine favorable rules for grouping the data, e.g., by attributes of a particular dimension.

In an embodiment, the supervised machine learning algorithm searches the positive data examples by performing a beam search on variance of specialized rules and evaluating candidate rules using different quality measures to minimize false positive and false negatives data example rates. The negative data examples generation algorithm generates distributed synthetic data examples for a rule to be specialized, and in the space defined by conditional parts of the rules and uniformly distributed.

In learning a rule, the algorithm starts with the most general rule, i.e., the empty rule wherein a single cluster covers the entire feature space including all positive and negative values and conducts a general-to-specific beam search. At each step of the search, the algorithm maintains a set of n best rules (rules with the largest F-measure scores, discussed below, where n is a user defined parameter. A smaller n translates into a smaller search space, hence a faster search. Each of the best rules can be further specialized by either adding new conditions or reducing the interval of a condition of a numeric attribute, as discussed with respect to FIG. 5. This search process repeats until the recalls of all rules are smaller than the minimum recall and the best rule is the rule generated by the rule search process.

The F-measure (also referred to as an F-score or the F1 score), is calculated using standard statistical techniques. It considers both the precision p and the recall r of the test to compute the score: p is the number of correct results divided by the number of all returned results and r is the number of correct results divided by the number of results that should have been returned. The F-measure can be interpreted as a weighted average of the precision and recall, where an F-measure reaches its best value at 1 and worst score at 0. The following formula is used to compute the F-measure score:

$$Fmeasure = \frac{\beta^2 + 1}{\frac{\beta^2}{recall} + \frac{1}{precision}}$$

Where $\beta^2 > 1$ favors more recall and $\beta^2 < 1$ favors more precision.

The F-measure is often used in the field of information retrieval for measuring search, document classification, and query classification performance. Earlier works focused primarily on the F-measure, but, with the proliferation of large scale search engines, performance goals changed to place more emphasis on either precision or recall and so is seen in wide application. In the case of the invention, the F-measure can be used to rank the most valuable clustering rules. This information provides predictive information on new, similar data and also helps to identify outlier data quickly.

In other embodiments of the invention, the rules can be determined with other known supervised learning algorithms. Such algorithms may be anything that can be expressed in terms of representation language. An example can be a physical object, a situation, a cause, or a concept. Training examples are usually described in one of the two types of representation languages: attribute-based or predicate-based. In an attribute-based representation, an example is represented as an n-tuple of attributes values, where n is a number of attributes. All n attributes define the event space. A domain is associated with each attribute used to describe examples. The domain indicates the values the attribute may assume. The values in a domain may be unordered (or nominal), ordered (or linear), or hierarchically structured.

Most supervised learning techniques generate models by detecting and describing similarities among positive examples and dissimilarities between positive and negative examples. Constructing such models from training examples involves the transformation of training examples using a set of refinement operators.

A refinement operator is either a specialization or a generalization operator. When applied to hypothesis or a training example, a generalization/specialization operator transforms it into a more general/special hypothesis. The algorithm described herein uses specialization operators to refine hypotheses.

Each hypothesis describes a subset of all examples, while all hypotheses representable in a given representation language form a hypothesis space. Learning can be viewed as a search process through the hypothesis space to find model of the target class. Generalization/specialization operators are search operators. Search heuristics are some preference criteria (also called biases). One of the most important description preference criteria is accuracy. Hypothesis accuracy depends on the completeness and consistency of this hypothesis with regard to the learning examples. Simplicity and comprehensibility are two other preference criteria. The supervised learning algorithm described herein uses an F-measure as a search heuristic preference criterion.

Figure 4:
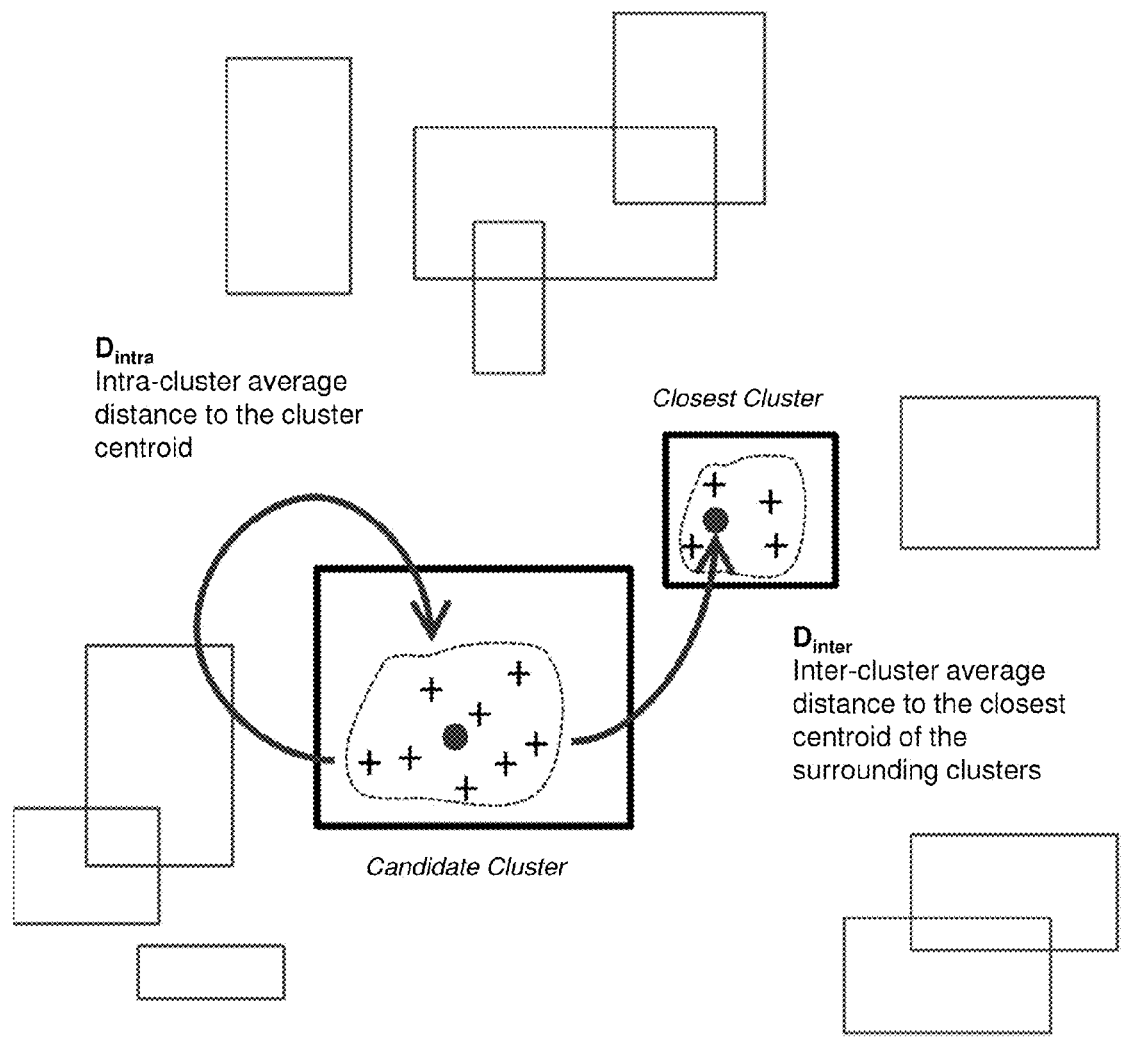
FIG. 4 illustrates the use of inter- and intra-cluster distance measurements for determining the quality of a rule set producing a cluster set.

Once a set of rules has been determined, the invention incorporates a distance-based computation using calculated centroids of the positive data examples to determine the quality of the clusters. This technique is shown graphically in FIG. 4. The centroid is a point in the representation space described by a given rule with the coordinates expressed by the numerical dimensions in the conditional parts of a rule and values representing arithmetic means of the positive data examples values described by the rule. In most systems, the centroid can be calculated by merely determining the weighted average of the position of the positive data in a cluster, however other techniques are known.

Once the centroid is determined, the Euclidean distance between each positive data point and the centroid is calculated and the values are used to estimate the average $D_{intra}$, the intra cluster distance (i.e., the average distance of positive data examples described by a rule to its centroid) as well as the $D_{inter}$, the distance between close neighboring rules, computed as the Euclidean distance between the cluster centroids. The generation of the $D_{intra}$ and $D_{inter}$ illustrated in FIG. 4.

Once $D_{intra}$ and $D_{inter}$ are calculated, the ratio of $D_{intra}$ and $D_{inter}$ is used to reject or merge rule clusters. The following are two cases for the candidate cluster rejection/acceptance. While other relationships can be used to validate rules, the following two rules are typically sufficient: 1) If ($D_{inter}$<P % of average interclass distance for already generated clusters, then the rule should be rejected. Otherwise the rule is accepted. P is a user defined number, and can be adjusted to optimize the spacing of the clusters. 2) If ($D_{intra}/D_{inter}$>=P % of average $D_{intra}/D_{inter}$ for already generated clusters, then the rule should be rejected. Otherwise the rule is accepted. Again P is a user defined number. With respect to the second rule P influences the size of the clusters relative to their spacing.

Data Analytics Using Assigned Clusters

Once the rules have been established using the above hybrid clustering algorithm, the clusters filled with positive data can be analyzed to spot trends or determine outliers. It should be appreciated that there are many different ways to evaluate the resulting grouping of data, and all of these analytical methods are encompassed by the invention. In particular, the methods disclosed by Meila can be used to evaluate the grouping. See Marina Meila, "Comparing Clusterings—An Information Based Distance," *Journal of Multivariate Analysis*, vol. 98, p. 873-895 (2007), incorporated by reference herein in its entirety. For example, using the centroids of the rules that survive the intra/inter distance test, it is possible to calculate a distribution of centroids and thus quickly identify clusters that are "far away", e.g., two standard deviations, from the mean centroid. Such clusters likely contain useful information of the sort discussed in the background, e.g., bad behavior or overlooked opportunity.

Figure 5:
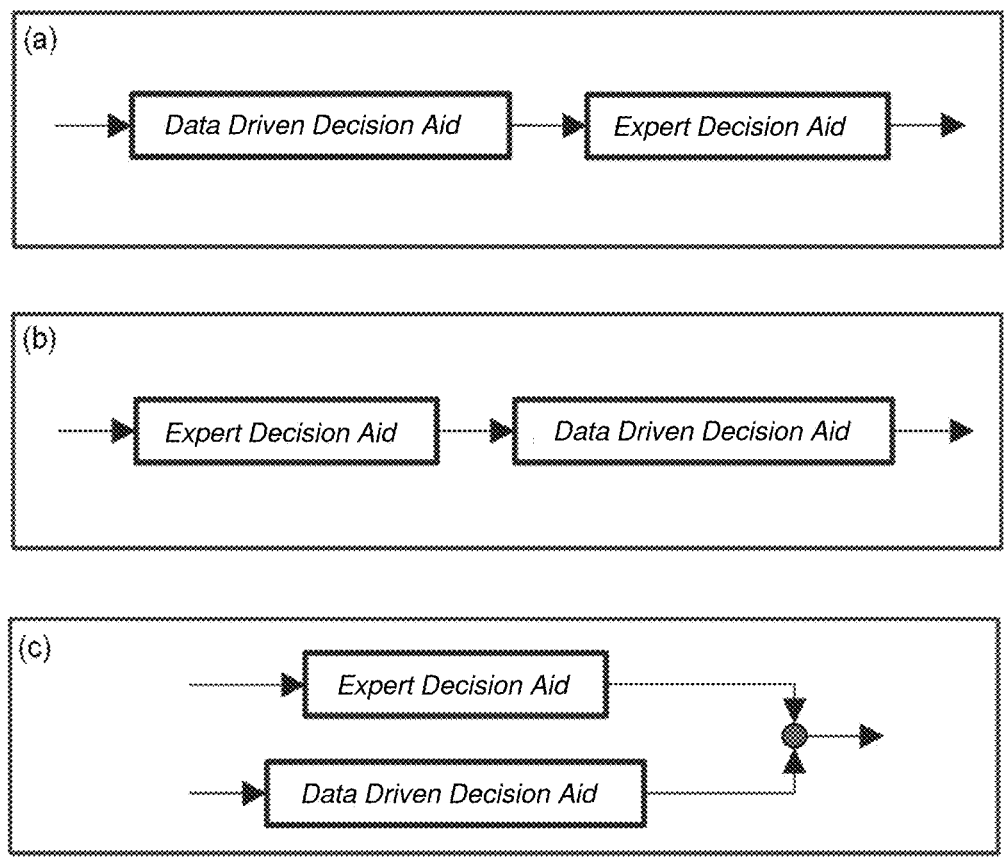
FIG. 5 shows three schemas that can be used in conjunction with the algorithms of the invention.

Additionally, the rules determined with the algorithms of the invention can be flavored with user input. The integration of data driven and expert-based decision aids can follow one of the three schemas, as illustrated in FIG. 5. In the first schema, —(a) where transactions of interest are checked against auditing guidelines to verify whether they represent a new piece of knowledge (unknown unknowns) or whether they can be identified in the existing auditing rule base knowledge, (b) where the data-driven decision aid is used as a post-processing decision aid to discover outlier clusters in segments of transactions recommended by the expert-based decision aid, and (c) where both decision aids contribute to the final outcome (i.e., identification of transactions of interest) using a decision-making fusion schema (e.g., weighted voting on decisions recommended by both decision aids). The different schemas can be applied to different scenarios. For example, (a) represents discovery of new knowledge, (b) represents the scenarios where the data-driven decision aid to reduce the rate of false positives, and (c) represents all general scenarios.

System Implementation

The invention discloses hybrid data clustering that can be used to group data and analyze the data based upon the grouping, for example to identify trends or outliers. In accordance with the invention, one or more computer software programs can be stored on or in one or more computer-readable data storage devices, and one or more processors of one or more computing systems can access that or those devices to execute the instructions that constitute the program(s) and thereby cause the computing system(s) to carry out the innovative hybrid data clustering methods or techniques described herein.

The instructions that make up the software program(s) can be written in any suitable programming language such as C++, C#, Java, or Python. The computer-readable storage devices can be any one or more tangible devices such as RAM, ROM, hard disk, flash memory, optical disk, and/or any other type of temporary or permanent data storage device or mechanism, or the computer readable storage devices may be located on a remote server of unknown composition (i.e., in the "cloud"). The processors of the computing systems can be general-purpose microprocessors such as those available from Intel Corporation, and the computing systems can be general-purpose computers or more specialized computers such as servers or workstations. The computing systems can be or include mobile computing systems such as phones, tablets or other hand-held computing systems, and the computing systems can run one or more operating systems such as those available from Microsoft Corporation, Apple Inc., and Linux Foundation. The computing systems may operate independently of an operating system by running atop a web interface.

Embodiments of the present invention can be used to analyze data collected by an entity for trends and/or outliers important to the entity. Such information can be collected by a variety of mechanisms. One such mechanism can be an enterprise-wide customer relationship management architecture. A customer relationship management system can collect data associated with customers, products, services, support, costs, revenue and employee information by the system's nature of being accessible to all aspects of an enterprise. Another mechanism can be a data feed based upon web crawling software or information services, such as stock price feeds or electronic medical records.

Those of skill in the relevant art will appreciate that the methods disclosed typically exceed human capacity to analyze using "only pencil and paper." For example, even simple calculations with a limited number of data points are difficult when each datapoint has many variables, e.g., at least three variables, e.g., at least five variables, e.g., at least ten variables, e.g., at least twenty variables. Accordingly, the disclosed methods are typically limited to applications that use a computer system, i.e., a system including a processor and memory containing instructions to be carried out on by the processor. Additionally, many applications of the methods require nearly-real-time analysis that would be impossible if not implemented with a computer. For example, online sales, securities transactions, currency transactions, and medical diagnostics may require nearly instantaneous analysis to be of value to a user. In fact, computer implementation would be obligatory in any instance where the information is transient, or the action is time-sensitive. Furthermore, in other implementations, the sheer volume of data is beyond the capacity of one or more humans to analyze with pencil and paper in their lifetimes. For example, correlating genetic markers with risk factors may require the characterization of billions of separate multivariable data points to determine an answer.

Figure 6:
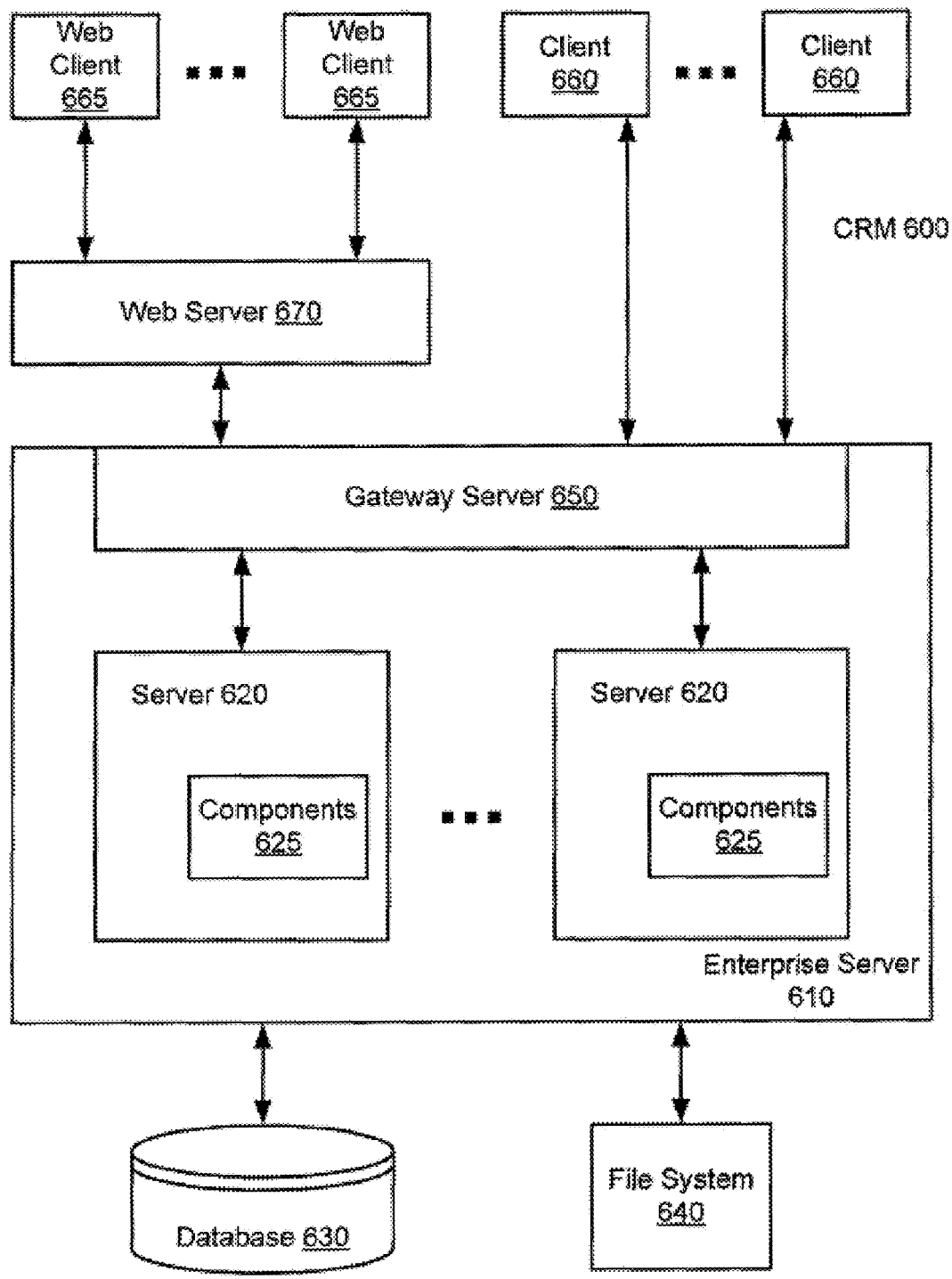
FIG. 6 shows an embodiment of a computer implemented system for defining clusters and analyzing the resulting clustered data.

FIG. 6 is a simplified block diagram illustrating a customer relationship management architecture usable in conjunction with embodiments of the present invention. The illustrated customer relationship management environment includes an enterprise server 610 that is a logical grouping of one or more servers 620 that support a group of clients (660, 665) accessing a common database 630. An enterprise server can be configured, managed and monitored as a single logical group, allowing an administrator to start, stop, monitor or set parameters for servers 620 within enterprise server 610. In such a configuration, parameters for the customer relationship management system can be set at the enterprise server level, and these parameters can apply to every server operating within the enterprise server. In addition, other parameters can be adjusted at a server (620) level to support fine tuning of those parameters. In this hierarchical parameter context, if a parameter is set at a server level, then the server-specific value for the parameter can override an enterprise server-level setting for the parameter. Further, parameter settings at a component level (processes executed on servers 620) will override those set at the server level.

A server 620 can support back-end and interactive processes for each client accessing the server. These processes are illustrated as one or more components 625 within each server. Examples of component processes include, for example, mobile web client synchronization, operation of business logic for web clients, connectivity and access to database and file system for clients, integration with legacy or third-party data (e.g., data not native to the customer relationship management (CRM) system), automatic assignment of new accounts, opportunities, service requests, and other records, and workflow management. Embodiments of rules-based decision-making modules can be associated with any of the component processes listed above. A server 620 can support, for example, multi-process and multi-threaded components, and can operate components in background, batch, and interactive modes. A server component can also operate on multiple servers 620 simultaneously to support an increased number of users or larger batched workloads.

In an embodiment, servers 620 are coupled to a gateway server 650 illustrated as part of enterprise server 610. Gateway server 650 can coordinate the operations of enterprise server 610 and servers 620. A gateway server can provide persistent storage of enterprise server configuration information, including, for example, definitions and assignments of component groups and components, operational parameters, and connectivity information. A gateway server can also serve as a registry for server and component availability information. For example, a server 620 within enterprise server 610 can notify gateway server 650 of availability. Connectivity information such as network addresses can be stored in a storage accessed by gateway server 650. If a server 620 shuts down or otherwise becomes unavailable, connectivity information related to that server can be cleared from gateway server 650.

Through their relationship in enterprise server 610, servers 620 and their components 625 access one or more databases 630 or file systems 640. CRM systems employing embodiments of the present invention can include as one or more components 625 the rules-based decision-making engine. Database 630 can store, for example, RDBM (relational database management) client software and tables, indexes, and data related to all operations impacted by the CRM system. Database information can include, for example, customer information, market data, historical pricing information, current pricing information, contact information, and the like. Similarly, file system 640 can store data and physical files used by clients 660 and 665 and enterprise server 610. File system 640 can be a shared directory, or set of directories on different devices, which is network accessible to all servers 620 in enterprise server 610. In order for a client to gain access to files in file system 640, a client can connect to an appropriate server 620 to request file uploads or downloads. Server 620 can then access file system 640 using, for example, a file system management component.

As stated above, embodiments of the clustering and data mining processes of the present invention can be implemented to execute on one or more of servers 620, accessing database 630 to store and retrieve data. An alternative embodiment provides a separate server accessible by the same or different web server. The separate server can provide access to database 630 or a copy thereof. The algorithms of the invention can also execute on one or more of clients 660 or web clients 665, accessing the database and file server information through gateway server 650.

Clients 660 and 665 provide access to enterprise server 610 for agents using the customer relationship management (CRM) system. Clients communicate to enterprise server 610 through gateway server 650 either directly (e.g., clients 660) or via a web server 670 (e.g., clients 665). A web server 670 can provide a mechanism by which enterprise server 610 can respond to web-based requests (e.g., HTML, XML, and the like). Web clients 665 can include clients coupled to web server 670 via a local area network, metro-area network or wide area network and propagated over a variety of communications media, as discussed above. Further, web clients 665 can include mobile clients accessing web server 670 through wireless communications means. Users of clients 660 and web clients 665 can include, for example, sales agents, service agents, customer representatives, managers of the business entity using the CRM, and the like.

As discussed above, the present invention can be implemented using a variety of computer systems and networks. An example of one such computing and network environment is described below with reference to FIGS. 7 and 8.

Figure 7:
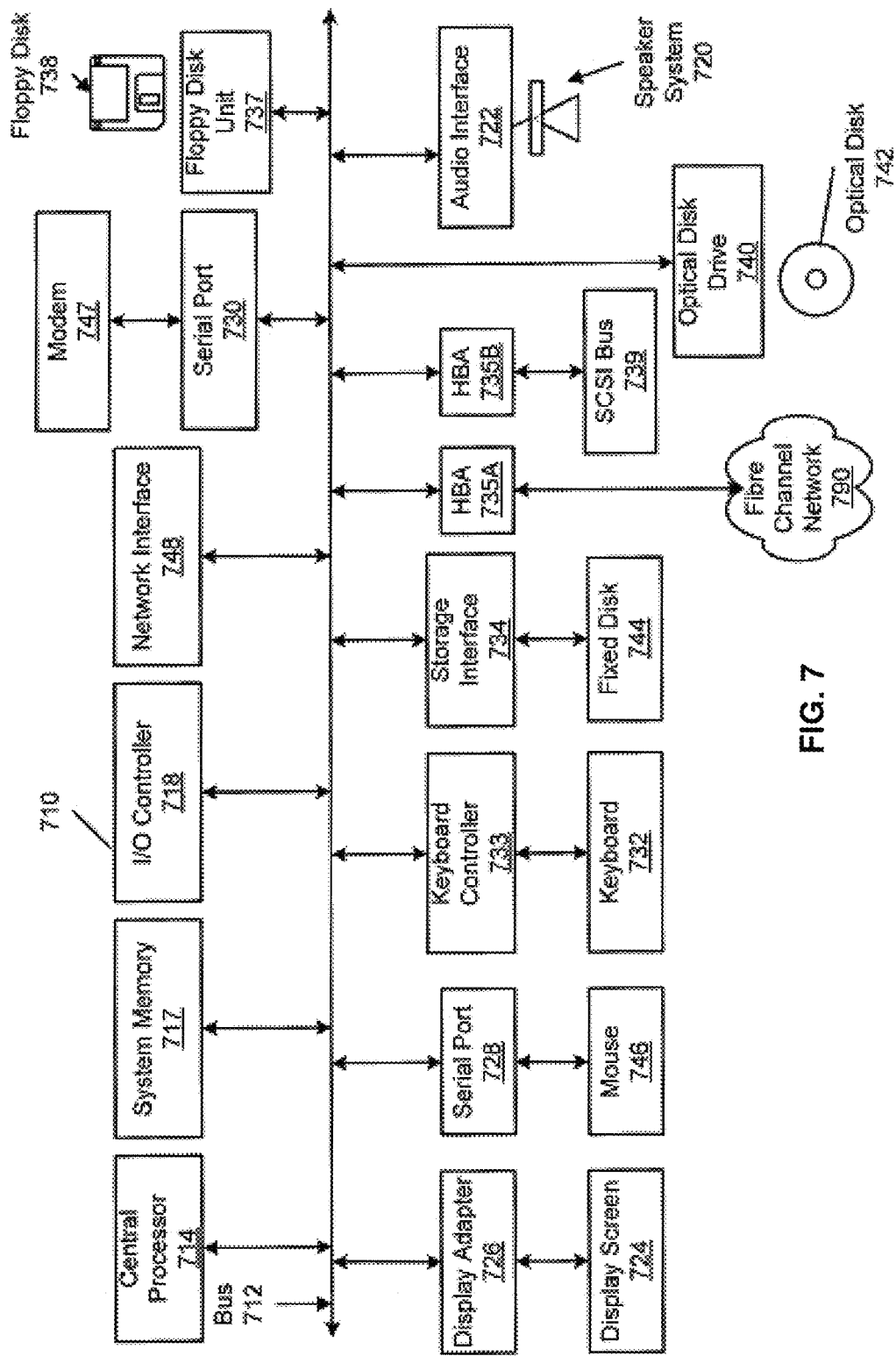
FIG. 7 shows an embodiment of a computer implemented system for defining clusters and analyzing the resulting clustered data.

FIG. 7 depicts a block diagram of a computer system 710 suitable for implementing aspects of the present invention (e.g., clients 660, web clients 665, and servers 620 and 670). Computer system 710 includes a bus 712 which interconnects major subsystems of computer system 710, such as a central processor 714, a system memory 717 (typically RAM, but which may also include ROM, flash RAM, or the like), an input/output controller 718, an external audio device, such as a speaker system 720 via an audio output interface 722, an external device, such as a display screen 724 via display adapter 726, serial ports 728 and 730, a keyboard 732 (interfaced with a keyboard controller 733), a storage interface 734, a floppy disk drive 737 operative to receive a floppy disk 738, a host bus adapter (HBA) interface card 735A operative to connect with a fiber channel network 790, a host bus adapter (HBA) interface card 735B operative to connect to a SCSI bus 739, and an optical disk drive 740 operative to receive an optical disk 742. Also included are a mouse 746 (or other point-and-click device, coupled to bus 712 via serial port 728), a modem 747 (coupled to bus 712 via serial port 730), and a network interface 748 (coupled directly to bus 712).

Bus 712 allows data communication between central processor 714 and system memory 717, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. Applications resident with computer system 710 are generally stored on and accessed via a computer-readable medium, such as a hard disk drive (e.g., fixed disk 744), an optical drive (e.g., optical drive 740), a floppy disk unit 737, or other storage medium. Additionally, applications can be in the form of electronic signals modulated in accordance with the application and data communication technology when accessed via network modem 747 or interface 748.

Storage interface 734, as with the other storage interfaces of computer system 710, can connect to a standard computer-readable medium for storage and/or retrieval of information, such as a fixed disk drive 744. Fixed disk drive 744 may be a part of computer system 710 or may be separate and accessed through other interface systems. Modem 747 may provide a direct connection to a remote server via a telephone link or to the Internet via an internet service provider (ISP). Network interface 748 may provide a direct connection to a remote server via a direct network link to the Internet via a POP (point of presence). Network interface 748 may provide such connection using wireless techniques, including digital cellular telephone connection, Cellular Digital Packet Data (CDPD) connection, digital satellite data connection or the like.

Many other devices or subsystems (not shown) may be connected in a similar manner. Conversely, all of the devices shown in FIG. 7 need not be present to practice the present invention. The devices and subsystems can be interconnected in different ways from that shown in FIG. 7. The operation of a computer system such as that shown in FIG. 7 is readily known in the art and is not discussed in detail in this application. Code to implement the present invention can be stored in computer-readable storage media such as one or more of system memory 717, fixed disk 744, optical disk 742, or floppy disk 738. The operating system provided on computer system 710 may be MS-DOS®, MS-WINDOWS®, APPLE®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present invention may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 8:
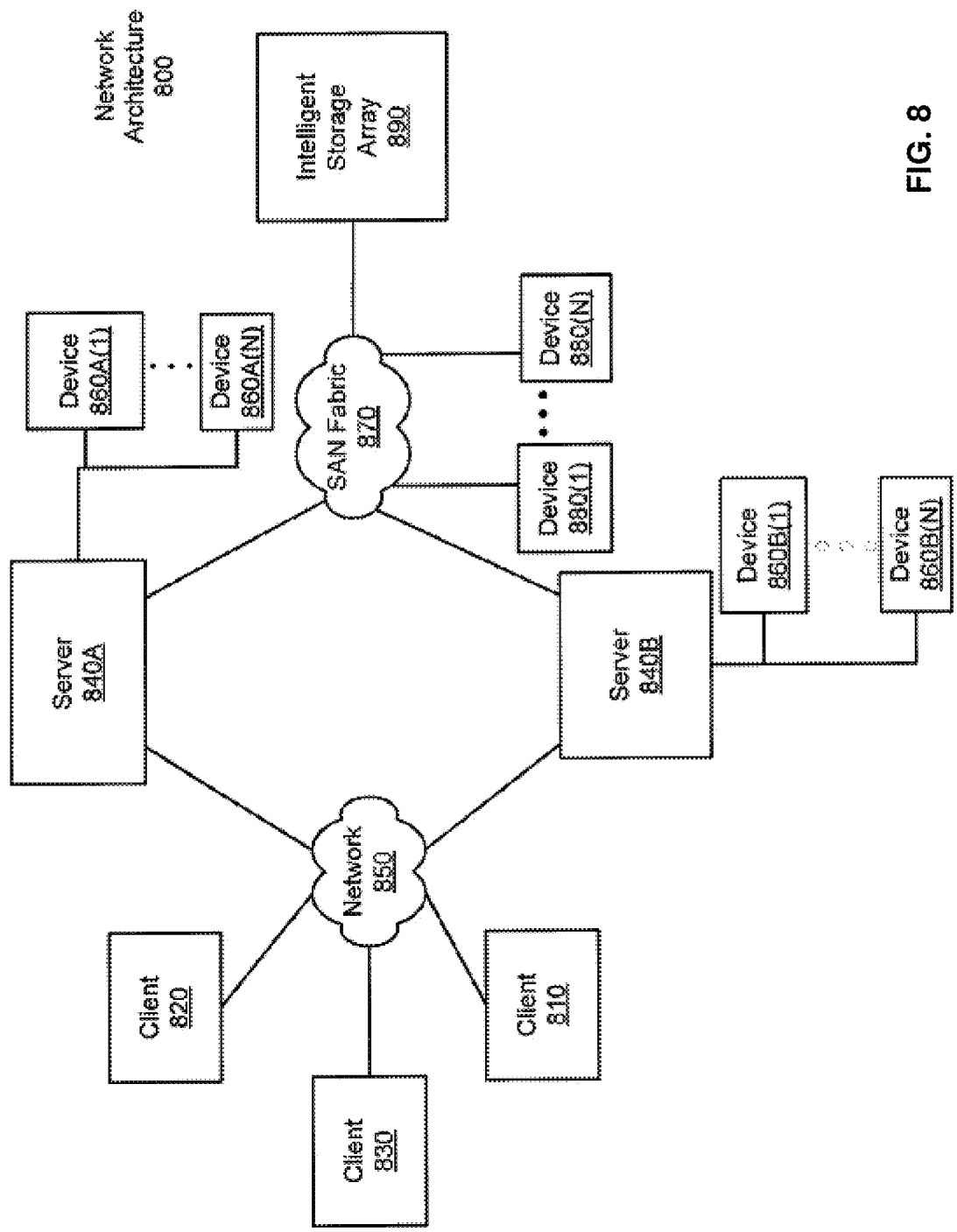
FIG. 8 illustrates three applications of the methods and systems of the invention via three different decision and integration schemas.

FIG. 8 is a block diagram depicting a network architecture 800 in which client systems 810, 820 and 830, as well as storage servers 840A and 840B (any of which can be implemented using computer system 710), are coupled to a network 850. Storage server 840A is further depicted as having storage devices 860A(1)-(N) directly attached, and storage server 840B is depicted with storage devices 860B(1)-(N) directly attached. Storage servers 840A and 840B are also connected to a SAN fabric 870, although connection to a storage area network is not required for operation of the invention. Storage area network (SAN) fabric 870 supports access to storage devices 880(1)-(N) by storage servers 840A and 840B, and so by client systems 810, 820 and 830 via network 850. Intelligent storage array 890 is also shown as an example of a specific storage device accessible via SAN fabric 870.

With reference to computer system 710, modem 747, network interface 748 or some other method can be used to provide connectivity from each of client computer systems 810, 820 and 830 to network 850. Client systems 810, 820 and 830 are able to access information on storage server 840A or 840B using, for example, a web browser or other client software (not shown). Such a client allows client systems 810, 820 and 830 to access data hosted by storage server 840A or 840B or one of storage devices 860A(1)-(N), 860B(1)-(N), 880(1)-(N) or intelligent storage array 890. FIG. 8 depicts the use of a network such as the Internet for exchanging data, but the present invention is not limited to the Internet or any particular network-based environment.

The present invention is well adapted to attain the advantages mentioned as well as others inherent therein. While the present invention has been depicted, described, and is defined by reference to particular embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described embodiments are examples only, and are not exhaustive of the scope of the invention.

The foregoing describes embodiments including components contained within other components (e.g., the various elements shown as components of computer system 710). Such architectures are merely examples, and, in fact, many other architectures can be implemented which achieve the same functionality. In an abstract but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components Likewise, any two components so associated can also be viewed as being "operably connected," or "operably coupled," to each other to achieve the desired functionality.

The foregoing detailed description has set forth various embodiments of the present invention via the use of block diagrams, flowcharts, and examples. It will be understood by those within the art that each block diagram component, flowchart step, operation and/or component illustrated by the use of examples can be implemented, individually and/or collectively, by a wide range of hardware, software, firmware, or any combination thereof. For example, specific electronic components can be employed in an application specific integrated circuit or similar or related circuitry for implementing the functions associated with one or more of the described functional blocks.

The present invention has been described in the context of fully functional computer systems; however, those skilled in the art will appreciate that the present invention is capable of being distributed as a program product in a variety of forms, and that the present invention applies equally regardless of the particular type of computer-readable media used to actually carry out the distribution. Examples of computer-readable media include computer-readable storage media, as well as media storage and distribution systems developed in the future.

The above description is intended to be illustrative of the invention and should not be taken to be limiting. Other embodiments within the scope of the present invention are possible. Those skilled in the art will readily implement the steps necessary to provide the structures and the methods disclosed herein, and will understand that the process parameters and sequence of steps are given by way of example only and can be varied to achieve the desired structure as well as modifications that are within the scope of the invention. Variations and modifications of the embodiments disclosed herein can be made based on the description set forth herein, without departing from the scope of the invention. Consequently, the invention is intended to be limited only by the scope of the appended claims, giving full cognizance to equivalents in all respects.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A computer implemented method for clustering data, the method comprising:
   (a) obtaining real data from a computer readable medium;
   (b) identifying a rule that clusters the real data, wherein identifying comprises:
      i) generating an evenly-distributed set of synthesized data having an identical number of points as the real data;
      ii) creating a database on the computer readable medium including the real data and the synthesized data;
      iii) executing a supervised machine-learning algorithm on a processor to determine a rule for clustering the real data, such that the real data is differentiated from the synthesized data:
      iv) clustering the real data using the determined rule;
      v) evaluating the quality of the determined rule for clustering the real data by:
         calculating a first quality statistic based on a percentage of the real data clustered by the rule; and
         calculating a second quality statistic based on a percentage of the real data and the synthesized data covered by the rule that is synthesized data;
         wherein a rule resulting in a larger first quality statistic and a smaller second quality statistic is evaluated more favorably than a rule resulting in a smaller first quality statistic and a larger second quality statistic;
      vi) correlating the clustered real data with a data space using a processor; and
      vii) validating the rule by comparing the location of the clustered real data with a location of other clustered real data using a processor;
   (c) clustering the real data with the rule using a processor; and
   (d) storing the clustered real data on the computer readable medium.

2. The method of claim 1, wherein validating comprises calculating a centroid of the clustered real data using a processor and calculating a distance between the centroid of the clustered real data and the centroid of a nearest neighboring cluster formed by the same rule.

3. The method of claim 2, wherein validating further comprises calculating an average distance between each real data point in the cluster and the centroid of the clustered real data.

4. The method of claim 3, further comprising calculating a ratio of (the average distance between each real data point in the cluster and the centroid) to (the distance between the centroid and the centroid of the nearest neighboring cluster formed by the same rule).

5. The method of claim 1, further comprising calculating a centroid for each cluster of real data on the computer readable medium, and comparing the distribution of centroids from the clusters of real data on the computer readable medium to determine a trend in the real data.

6. The method of claim 1, further comprising calculating a centroid for each cluster of real data on the computer readable medium, and comparing the distribution of centroids from the clusters of real data on the computer readable medium to determine an outlier in the real data.

7. The method of claim 1, wherein the real data relates to genetic sequences.

8. The method of claim 1, wherein the real data relates to stock, commodity, currency, or retail sales.

9. The method of claim 1, wherein the real data relates to athletic performance.

10. The method of claim 1, wherein the real data is data reported to a government authority.

11. A system for clustering data comprising a processor, memory, and a computer readable medium, wherein the computer readable medium comprises instructions that when executed cause the processor to:
   obtain real data from the computer readable medium;
   identify a rule that clusters the real data, wherein identifying comprises:
   i) generating an evenly-distributed set of synthesized data having an identical number of points as the real data;
   ii) creating a database on the computer readable medium including the real data and the synthesized data;
   iii) executing a supervised machine-learning algorithm to determine a rule for clustering the real data, such that the real data is differentiated from the synthesized data;
   iv) clustering the real data using the determined rule;
   v) evaluating the Quality of the determined rule for clustering the real data by:
      calculating a first quality statistic based on a percentage of the real data clustered by the rule; and
      calculating a second quality statistic based on a percentage of the real data and the synthesized data covered by the rule that is synthesized data;
   vi) correlating the clustered real data with a data space; and
   vii) validating the rule by comparing the location of the clustered real data with a location of other clustered real data;
   cluster the real data with the rule; and
   store the clustered real data on the computer readable medium.

12. The system of claim 11, wherein validating comprises calculating a centroid of the clustered real data and calculating a distance between the centroid of the clustered real data and the centroid of a nearest neighboring cluster formed by the same rule.

13. The system of claim 12, wherein validating further comprises calculating an average distance between each real data point in the cluster and the centroid of the clustered real data.

14. The system of claim 13, further comprising calculating a ratio of (the average distance between each real data point in the cluster and the centroid) to (the distance between the centroid and the centroid of the nearest neighboring cluster formed by the same rule).

15. The system of claim 11, wherein the computer readable medium further comprises instructions that cause the processor to calculate a centroid for each cluster of real data on the computer readable medium, and compare the distribution of centroids from the clusters of real data on the computer readable medium to determine a trend in the real data.

16. The system of claim 11, wherein the computer readable medium further comprises instructions that cause the processor to calculate a centroid for each cluster of real data on the computer readable medium, and compare the distribution of centroids from the clusters of real data on the computer readable medium to determine an outlier in the real data.

17. The system of claim 11, wherein the real data relates to genetic sequences.

18. The system of claim 11, wherein the real data relates to stock, commodity, currency, or retail sales.

19. The system of claim 11, wherein the real data relates to athletic performance.

20. The system of claim 11, wherein the real data is data reported to a government authority.

* * * * *